United States Patent
Sprenger et al.

(10) Patent No.: US 7,518,719 B2
(45) Date of Patent: Apr. 14, 2009

(54) CONTAMINANT ANALYZER FOR FUEL

(75) Inventors: Greg Sprenger, Colorado Springs, CO (US); Jed Stevens, Colorado Springs, CO (US); Michael White, Arlington, MA (US); Richard Hillis, Quincy, MA (US); Jacob Lavenberg, Somerville, MA (US); Chris Templeman, Somerville, MA (US)

(73) Assignee: Velcon Filters, Inc., Colorado Springs, CO (US)

( * ) Notice: Subject to any disclaimer, the term of this patent is extended or adjusted under 35 U.S.C. 154(b) by 155 days.

(21) Appl. No.: 11/627,105

(22) Filed: Jan. 25, 2007

(65) Prior Publication Data

US 2007/0175269 A1  Aug. 2, 2007

Related U.S. Application Data

(60) Provisional application No. 60/762,831, filed on Jan. 27, 2006.

(51) Int. Cl.
  *G01J 1/10* (2006.01)
(52) U.S. Cl. .................. 356/243.2; 356/339; 356/343; 356/70

(58) Field of Classification Search ......... 356/336–343, 356/243.1–243.8; 367/70, 432–440
See application file for complete search history.

(56) References Cited

U.S. PATENT DOCUMENTS

| | | | |
|---|---|---|---|
| 3,289,003 A * | 11/1966 | Jorgenson | 250/565 |
| 3,528,546 A | 9/1970 | McPherson | |
| 3,892,485 A * | 7/1975 | Merritt et al. | 356/339 |
| 4,432,645 A * | 2/1984 | Frungel | 356/338 |
| 4,574,833 A | 3/1986 | Custer | |
| 5,200,064 A * | 4/1993 | Russ et al. | 210/94 |
| 5,343,156 A | 8/1994 | Johnson et al. | |
| 5,350,922 A | 9/1994 | Bartz | |
| 5,576,482 A * | 11/1996 | Russ et al. | 73/61.43 |
| 6,657,722 B1 * | 12/2003 | Nagayoshi | 356/326 |
| 6,783,705 B1 * | 8/2004 | Leveille | 252/588 |
| 6,978,210 B1 | 12/2005 | Suter et al. | |

* cited by examiner

*Primary Examiner*—Hoa Q Pham
(74) *Attorney, Agent, or Firm*—Fraser Clemens Martin & Miller LLC; Donald R. Fraser

(57) ABSTRACT

A method and apparatus for detecting contaminants in hydrocarbon fuel are disclosed, wherein a fuel analyzer includes a flow sensor to facilitate an automatic start up and shut down of a fuel analysis, and a calibration standard to facilitate an inline calibration of the fuel analyzer.

11 Claims, 1 Drawing Sheet

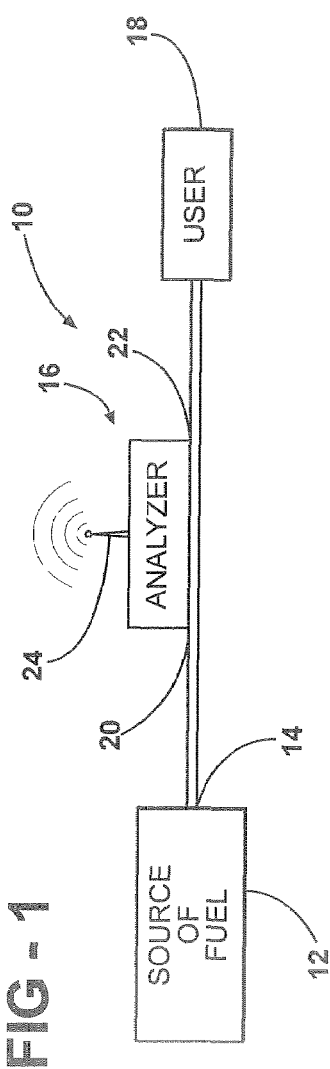
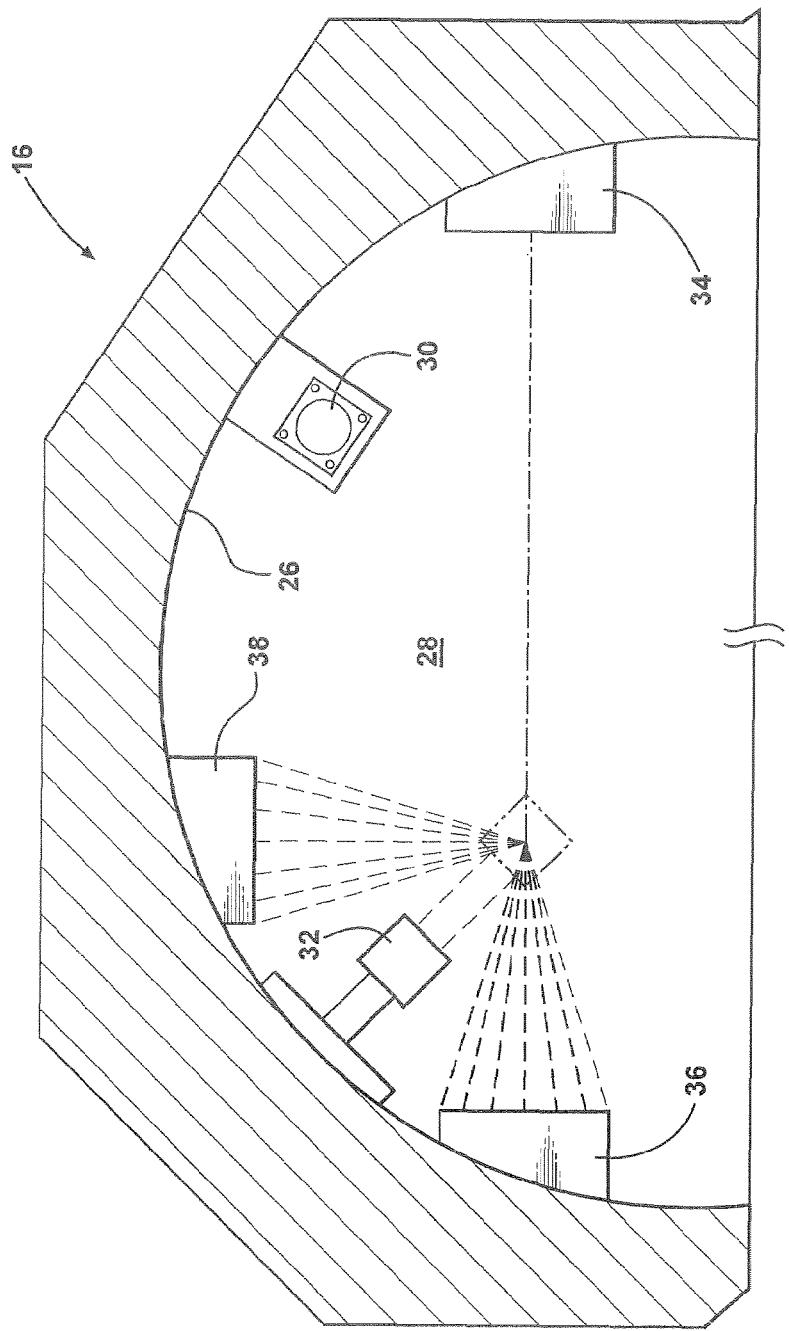

CONTAMINANT ANALYZER FOR FUEL

CROSS-REFERENCE TO RELATED APPLICATION

This application claims the benefit of U.S. Provisional Patent Application Ser. No. 60/762,831 filed Jan. 27, 2006.

BACKGROUND OF THE INVENTION

1. Field of the Invention

The present invention relates to a method and apparatus for detecting contaminants in hydrocarbon fuel and more particularly to a method and apparatus for inline use to detect the presence of water and particulate contaminants in hydrocarbon fuels during the transfer of the fuel.

2. Description of the Prior Art

Various types of systems are available for the analysis of fuel to determine the presence of water and particulate contaminants. Typically the existing systems utilize apparatus requiring a manual operation wherein an operator is required to manually initiate the operation of the system and to standby during the operational cycle thereby preventing the performance of any other duties during the transfer of the fuel. Most of the known systems for analyzing fuel require the apparatus to be manually calibrated which necessitates the physical removal of the inline instrument from service. Manifestly, such procedures are costly, difficult, and time-consuming.

It is an object of the present invention to produce a method and apparatus for automatically detecting contaminants, such as water and particulates, in transient fuel which can be operated without an attending operator Another object of the present invention is to produce a method and apparatus for detecting contaminants in transient fuel which commences operation simultaneously with the commencement of the flow of the fuel to be analyzed.

Still another object of the invention is to produce a method and apparatus to automatically analyze hydrocarbon fuel as the fuel is caused to flow from one point to another and to automatically produce a signal upon the detection of contamination.

Yet another object of the present invention is to produce a method and apparatus for automatically calibrating a fuel analyzing system without a physical removal of the apparatus from service.

SUMMARY OF THE INVENTION

It has been surprisingly determined that the above, as well as other, objects and advantages of the invention may be achieved by a method for inline contamination analysis of transient fuel comprising the steps of: providing a source of fuel to be analyzed; causing the fuel to flow from the source to a point remote therefrom; analyzing the transient fuel for contamination; and producing a signal upon sensing the presence of contaminants therein.

Also, it has been surprisingly determined that the following system is effective for carrying out the above method wherein there is provided a source of fuel to be analyzed; means for conveying fuel from the source to a point remote from the source; a detector for analyzing the water and particulate contamination in the transient fuel; a sensor for sensing the flow of fuel from the source including actuating means for effecting actuation of the detector; and signal producing means operatively coupled to the detector for producing a signal upon a predetermined quantitative detection of contaminants in the transient fuel by the detector.

BRIEF DESCRIPTION OF THE DRAWINGS

The above objects and advantages of the invention will become readily apparent to one skilled in the art from reading the following description of an embodiment of the invention when considered in the light of the accompanying drawings in which:

FIG. 1 is a schematic block diagram of a system utilizing the present invention;

FIG. 2 is a cross-sectional view of an optical sensor and calibration standard incorporated in the analyzer of the system of FIG. 1.

DETAILED DESCRIPTION OF THE PREFERRED EMBODIMENT OF THE INVENTION

The following detailed description and appended drawings describe and illustrate various exemplary embodiments of the invention. The description and drawings serve to enable one skilled in the art to make and use the invention, and are not intended to limit the scope of the invention in any manner. In respect of the methods disclosed and illustrated, the steps presented are exemplary in nature, and thus, the order of the steps is not necessary or critical.

FIG. 1 illustrates, in schematic form, a system 10 for accomplishing the invention. More specifically, there is provided a source of fuel 12 having an outlet 14 in communication with a fuel analyzer 16, and a user 18 positioned remotely therefrom. It will be understood that fuel analyzer 16 may be located at a distance from the outlet 14 of the source of fuel 12. The location is not deemed critical, other than it must be located at a position enabling the flowing fuel to be analyzed.

The fuel analyzer 16 includes a first end 20, a spaced apart second end 22, and a data transmitter 24. As shown in FIG. 2, an inner wall 26 of the analyzer 16 forms a flow chamber 28 therein.

A flow sensor 30 is disposed on the inner wall 26 and extends into the flow chamber 28. The flow sensor 30 includes a means for sensing a flow of fluid.

A calibration standard 32 is disposed on the inner wall 26 and extends into the flow chamber 28. As shown in FIG. 2, the calibration standard 32 is extendable from a first position represented by dashed lines, to a second position represented by solid lines. The first position lies at an intersection point of an optical signal 34, a forward scatter sensor 36, and a ninety degree scatter sensor 38, hereinafter referred to as the sensing zone. In the embodiment shown, the optical signal 34 and the forward scatter sensor 36 lie in substantially the same plane as the calibration standard 32 while in the first position. It is understood that the optical signal 34 and the forward scatter sensor 36 can lie in different planes as desired. The second position does not lie in the same plane as the optical signal 34 and the forward scatter sensor 36. It should be understood that the optical sensor 34 is a light source for producing a beam of light.

The calibration standard 32 shown in FIG. 2 is cube-shaped and is formed from glass. It is understood that the calibration standard 32 can be other shapes and formed from other materials as desired. The calibration standard 32 includes a series of inclusions (not shown) or imperfections formed on a surface thereof.

In use, a fuel is caused to flow from the source of fuel 12 into the first end 20 of the fuel analyzer 16. The flow sensor 30 senses the fuel and initiates operation of the fuel analyzer 16.

During the initial flow of fuel, air bubbles may be present in the flowing fuel. Due to the possibility of air bubbles in the stream of fuel, a time delay can be incorporated to eliminate transient conditions in the fuel. At the expiration of the selected time delay, the analyzation of the fuel begins and will continue until the flow of fuel from the source of fuel 12 into the fuel analyzer 16 is stopped. When the flow of fuel is stopped, the flow sensor 30 detects such condition and stops the analysis of the fuel.

During the fuel analysis, the optical signal 34 transmits a predetermined amount of light toward the forward scatter sensor 36. If a solid contaminant (not shown) is contained in the fuel flowing through the flow chamber 28 between the optical signal 34 and the forward scatter sensor 36, a portion of the light from the optical signal 34 is reflected to the ninety degree scatter sensor 38. If a liquid contaminant (not shown) is contained in the fuel flowing through the flow chamber 28 between the optical signal 34 and the forward scatter sensor 36, a portion of the light from the optical signal 34 is refracted to the forward scatter sensor 36. The forward scatter sensor 36 and the ninety degree scatter sensor 38 generate data based on light readings taken from the optical signal 34. The data transmitter 24 sends the data from the forward scatter sensor 36 and the ninety degree scatter sensor 38 to a data gathering device (not shown), which receives and gathers the data. The user 18 can thereafter manipulate the data as desired.

In the event that a calibration of the fuel analyzer 16 is desired, the calibration standard 32 is positioned by the energization of an associated motor (not shown) or solenoid operated cylinder (not shown). When in the sensing zone, the calibration standard 32 lies in the plane shared by the optical signal 34 and the forward scatter sensor 36. The light from the optical signal 34 refracts from the inclusions or imperfections formed on the calibration standard 32 to the forward scatter sensor 36. Additionally, the light from the optical signal 34 reflects from the inclusions or imperfections formed on the calibration standard 32 to the ninety degree scatter sensor 38. Calibrating scatter readings are taken by the forward scatter sensor 36 and the ninety degree scatter sensor 38 based on the light from the optical signal 34. The readings are then compared to predetermined calibration readings. If the actual readings are not equal the predetermined calibration readings, the fuel analyzer 16 is calibrated accordingly. Upon completion of the calibration process, the calibration standard 32 is moved from the sensing zone to the second position, allowing the fuel analyzer 16 to operate normally.

Since the calibration standard 32 is permanently located within the fuel analyzer 16, calibration can be conducted frequently without disrupting the operation of the fuel analyzer 16. Calibration may be set to operate randomly or automatically, such as at certain time intervals, as a function upon the occurrence of a predetermined number of data gathering occurrences, for example.

In order to maintain consistency, the calibration standard 32 may be positioned in a turbulent section of the fluid flow being sensed. Such positioning tends to flush away any contamination that may have accumulated thereon from the calibration standard 32. Thereby, the consistency of measurement is maintained.

It is to be noted that typically inline instrumentation for analysis of transient fluids requires calibration necessitating the removal of the instruments. Removal from the piping disrupts the operation of the system and, therefore, it is desirable to provide an alternative. As described above, the fuel analyzer 16 illustrated in FIG. 2 is effective in achieving the desired results.

A new fuel analyzer 16 has been described which includes a flow sensor 30 for initiating operation of a fuel analysis, the gathering of data, and the discontinuance of the data gathering. In addition, a method is described for automatically calibrating the fuel analyzer 16 between uses thereof. A calibration standard 32 is automatically inserted into an optical path to create standard light scattering signals used to calibrate the fuel analyzer 16. The calibration standard 32 is moved from the sensing position to permit normal analysis of the fuel.

From the foregoing description, one ordinarily skilled in the art can easily ascertain the essential characteristics of this invention and, without departing from the spirit and scope thereof, can make various changes and modifications to the invention to adapt it to various usages and conditions.

What is claimed is:

1. Apparatus for analyzing fuel comprising:
   means for conveying fuel from a source along a path;
   means for analyzing the fuel being conveyed for at least one of water contamination and particulate contamination in the fuel, the means for analyzing the fuel including a light source for producing a beam, and at least one of a forward scatter sensor and a ninety degree scatter sensor; and
   means for selectively calibrating the means for analyzing the fuel including a calibration standard movable to and from a sensing zone of the means for analyzing, the calibration standard selectively refracting the beam causing a portion thereof to be directed to the forward scatter sensor and another portion thereof to be directed to the ninety degree scatter sensor to create a selected scattering signal for calibrating the means for analyzing the fuel.

2. Apparatus defined in claim 1, including a sensor for sensing the flow of fuel.

3. Apparatus defined in claim 2, wherein the sensor is disposed within the means for conveying fuel.

4. Apparatus defined in claim 1, wherein the means for calibrating is disposed within the means for conveying fuel.

5. Apparatus defined in claim 4, wherein the means for calibrating is positioned within an area of turbulent flow of the fuel flowing through the means for conveying fuel.

6. Apparatus defined in claim 1, wherein the means for calibrating functions upon at least one of a predetermined amount of time and a predetermined number of analysis cycles.

7. Apparatus defined in claim 1, including a means for transmitting analysis data to a data gathering device.

8. Apparatus defined in claim 1, wherein the means for calibrating is generally cube shaped.

9. Apparatus defined in claim 1, wherein the means for calibrating is formed from glass.

10. Apparatus defined in claim 1, wherein the means for calibrating includes at least one inclusion.

11. Apparatus defined in claim 1, wherein the means for calibrating includes at least one surface imperfection.

* * * * *